US012667637B2

(12) United States Patent
Lambert et al.

(10) Patent No.: US 12,667,637 B2
(45) Date of Patent: *Jun. 30, 2026

(54) DOOR LATCH, LOCK AND OPEN MECHANISM FOR MEDICAL DEVICE TREATMENT SYSTEM

(71) Applicant: American Sterilizer Company, Mentor, OH (US)

(72) Inventors: Sean Lambert, Wickliffe, OH (US); Sandeepan Dutta, Lyndhurst, OH (US); Ethan K. Lange, Painesville, OH (US); Christopher J. Wiet, Torrance, CA (US); Michael Rabinovich, Solon, OH (US)

(73) Assignee: American Sterilizer Company, Mentor, OH (US)

( * ) Notice: Subject to any disclaimer, the term of this patent is extended or adjusted under 35 U.S.C. 154(b) by 153 days.

This patent is subject to a terminal disclaimer.

(21) Appl. No.: 18/631,411

(22) Filed: Apr. 10, 2024

(65) Prior Publication Data

US 2024/0252706 A1 Aug. 1, 2024

Related U.S. Application Data

(63) Continuation of application No. 17/007,289, filed on Aug. 31, 2020, now Pat. No. 11,980,697.

(Continued)

(51) Int. Cl.
*A61L 2/24* (2006.01)
*E05B 47/00* (2006.01)
(Continued)

(52) U.S. Cl.
CPC ............ *A61L 2/24* (2013.01); *E05B 47/0004* (2013.01); *E05B 47/023* (2013.01); *E05F 15/73* (2015.01);
(Continued)

(58) Field of Classification Search
CPC ........ A61L 2/24; A61L 2/26; A61L 2202/122; A61L 2202/121; E05F 15/73;
(Continued)

(56) References Cited

U.S. PATENT DOCUMENTS

| | | | |
|---|---|---|---|
| 3,751,088 A | 8/1973 | Schlage et al. | |
| 3,767,242 A | 10/1973 | Quantz | |

(Continued)

FOREIGN PATENT DOCUMENTS

| | | |
|---|---|---|
| CN | 106121384 B | 5/2018 |
| CN | 208710104 U | 4/2019 |

(Continued)

OTHER PUBLICATIONS

Extended European Search Report for corresponding EP Application No. 24200342.4 dated Jan. 7, 2025.

(Continued)

*Primary Examiner* — Lessanework Seifu
(74) *Attorney, Agent, or Firm* — Renner, Otto, Boisselle & Sklar, LLP

(57) ABSTRACT

A latch and lock assembly includes a lever pivotable between a latched and unlatched position. A first actuator selectively moves a locking tab between a locked and unlocked position. In the locked position, the locking tab blocks pivotable movement of the lever from the latched position to the unlatched position. In the unlocked position, the locking tab allows pivotable movement of the lever from the latched position to the unlatched position. A second actuator selectively rotates a door opening tab between a first and second position when the locking tab is in the unlocked position is included. When the door opening tab is in the first position the lever is in a latched position, and when the door opening tab is rotated from the first position to the second position, the door opening tab abuts the lever and urges the lever from the latched position to the unlatched position.

10 Claims, 8 Drawing Sheets

Related U.S. Application Data

(60) Provisional application No. 62/899,192, filed on Sep. 12, 2019.

(51) Int. Cl.

| | |
|---|---|
| *E05B 47/02* | (2006.01) |
| *E05F 15/73* | (2015.01) |
| *A61L 103/05* | (2026.01) |
| *A61L 103/15* | (2026.01) |

(52) U.S. Cl.
CPC ....... *A61L 2103/05* (2026.01); *A61L 2103/15* (2026.01); *A61L 2202/122* (2013.01); *A61L 2202/17* (2013.01); *E05B 2047/0007* (2013.01); *E05Y 2400/858* (2013.01)

(58) Field of Classification Search
CPC .............. E05B 47/0004; E05B 47/023; E05B 47/0001; E05B 57/00; E05B 2047/0007
See application file for complete search history.

(56) References Cited

U.S. PATENT DOCUMENTS

| | | | |
|---|---|---|---|
| 3,874,117 | A | 4/1975 | Boehm |
| 4,434,635 | A | 3/1984 | Borgato |
| 5,009,034 | A | 4/1991 | Schneider et al. |
| 5,223,229 | A | 6/1993 | Brucker |
| 5,263,596 | A | 11/1993 | Williams |
| 5,460,294 | A | 10/1995 | Williams |
| 5,879,036 | A | 3/1999 | Moline et al. |
| 7,038,409 | B1 | 5/2006 | Mullet |
| 7,068,179 | B2 | 6/2006 | Snell et al. |
| 9,714,230 | B2 | 7/2017 | Nie |
| 10,010,236 | B2 | 7/2018 | Alexander |
| 2003/0222548 | A1 | 12/2003 | Richardson et al. |
| 2013/0219793 | A1 | 8/2013 | O'Rourke |
| 2014/0265805 | A1 | 9/2014 | Chamberlin |
| 2015/0073666 | A1 | 3/2015 | Dotterweich et al. |

FOREIGN PATENT DOCUMENTS

| | | |
|---|---|---|
| EP | 1 405 967 A1 | 4/2004 |
| EP | 2578426 B1 | 8/2015 |
| JP | 2011206157 A | 10/2011 |
| WO | 1993006325 A1 | 4/1993 |

OTHER PUBLICATIONS

Invitation to Pay Additional Fees for corresponding International Application PCT/US2020/048705, dated Dec. 4, 2020.

International Search Report and Written Opinion for corresponding International Application PCT/US2020/048705, dated Mar. 25, 2021.

Second Written Opinion of the International Preliminary Examining Authority for corresponding International Application PCT/US2020/048705, mailed Aug. 12, 2021.

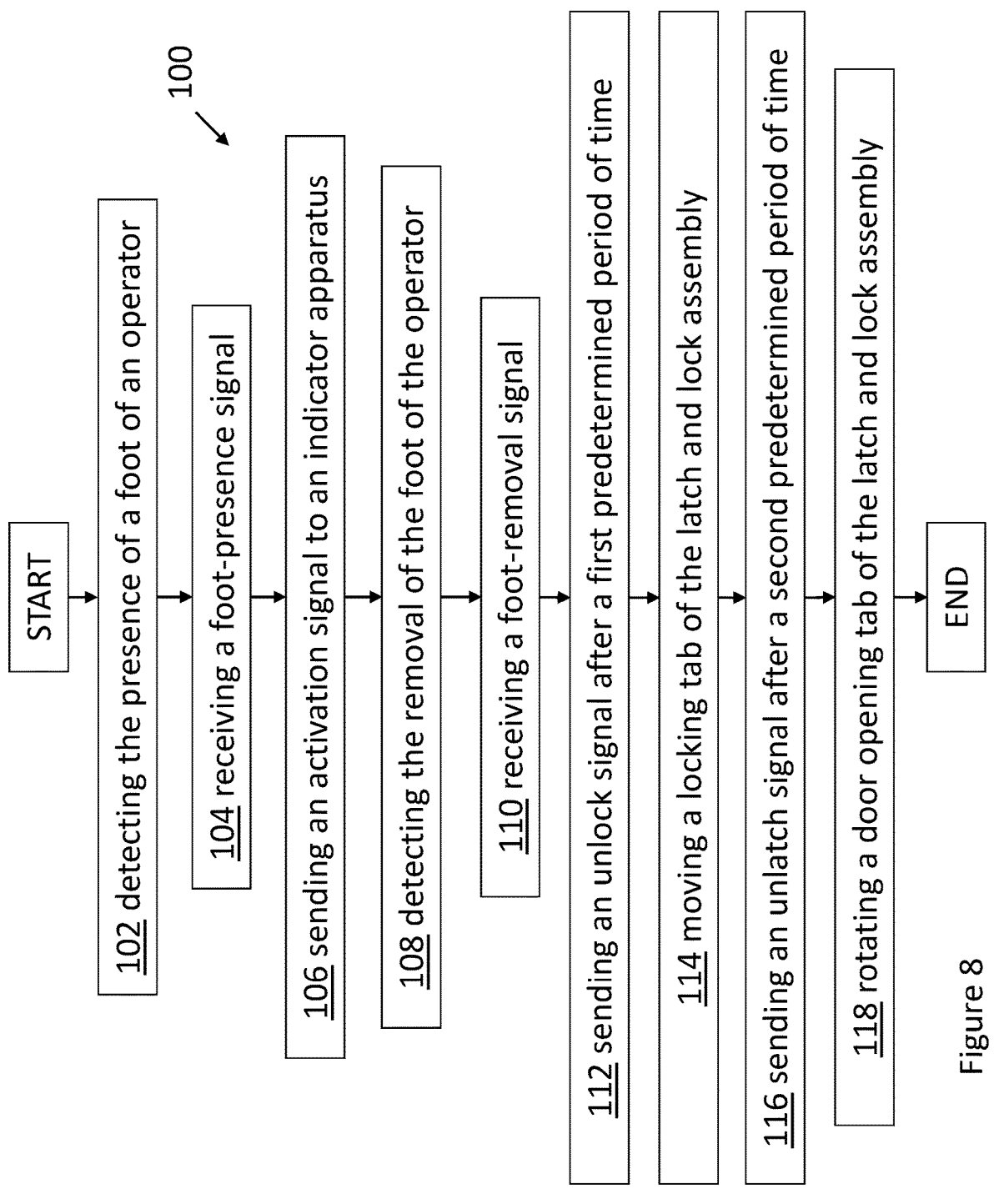

100

START 102 detecting the presence of a foot of an operator 104 receiving a foot-presence signal 106 sending an activation signal to an indicator apparatus 108 detecting the removal of the foot of the operator 110 receiving a foot-removal signal 112 sending an unlock signal after a first predetermined period of time 114 moving a locking tab of the latch and lock assembly 116 sending an unlatch signal after a second predetermined period of time 118 rotating a door opening tab of the latch and lock assembly

END

Figure 8

DOOR LATCH, LOCK AND OPEN MECHANISM FOR MEDICAL DEVICE TREATMENT SYSTEM

RELATED APPLICATION DATA

This application is a continuation of U.S. application Ser. No. 17/007,289 filed Aug. 31, 2020, which claims the benefit of U.S. Provisional Application No. 62/899,192, filed Sep. 12, 2019, which are incorporated herein by reference in their entireties.

FIELD OF THE INVENTION

The technology of the present disclosure relates generally to medical device treatment systems, and more particularly to methods and mechanisms for latching, locking and opening a door or lid of such medical device treatment systems.

BACKGROUND

Prevention of contamination has always been a challenge in the medical device industry. Conventional medical device treatment systems, such as washers, disinfectors or sterilizers (WDS) are available to wash, disinfect and/or sterilize medical devices, but are not capable of disinfecting or sterilizing their own exterior surfaces. In particular, WDS doors and/or lids may trap and harbor harmful or toxic contaminants and/or germs when an operator manually opens or closes the door and/or lid to load or unload medical devices into or out from the WDS. Accordingly, hands-free operation of WDS doors and/or lids is advantageous in the medical device industry to prevent such contamination.

Various standards in the medical device industry require that WDS doors and/or lids remain locked during sterilization or disinfection cycles. Typical hands-free operation may therefore include automatic door latching, locking, opening and/or closing. Conventionally, however, these operations require two or more independent mechanisms to control door latching, locking, opening or closing. For example, some conventional medical device treatment systems have mechanisms that open or close the door, but require a separate mechanism to latch or lock the door. As a result of two independent mechanisms, conventional assemblies are generally quite complex and expensive and are typically too large for installation in smaller WDS's.

Various other problems exist in locking, latching and opening assemblies of conventional medical device treatment systems. For example, some automatic door opening mechanisms operate to open the door immediately upon activation of a door opening sensor. Operators, therefore, may not have enough time to step back and allow space for the door to open.

Additionally, many conventional WDS latching mechanisms use open hook grab latches which can be overcome with excessive downward force on the door, even when the door latch mechanism is in a locked state. This excessive force may impart undue stress on the fragile components of the door latch mechanism and may cause irreversible damage. To compensate for this, heavy-duty, stronger mechanism components and door hinges have been used to increase the amount of force required to overcome the latches to levels beyond that typically achievable by an operator. For smaller medical device treatment systems, however, using heavy-duty components and hinges is not feasible due to space constraints.

SUMMARY OF INVENTION

The present disclosure, therefore, relates to a medical device treatment system including a door latch, lock and open mechanism having automatic and manual door opening features, all fully integrated into one assembly. The door latch, lock and open mechanism assembly provides enough adjustability to handle manufacturing tolerances, while also retaining the adjustment throughout its service life. In certain embodiments, the medical device treatment system may include one or more of the following features: 1) a single mechanism that can latch, lock and open a medical device treatment system door, 2) a hands-free, foot-operated control mechanism to detect when the operator wishes to open the door automatically, and 3) a forced-entry prevention mechanism to ensure the operator cannot open the door using excessive physical force when the door is closed, latched and locked.

Accordingly, in one aspect of the invention a latch and lock assembly is provided. The latch and lock assembly includes a lever pivotable between a latched position and an unlatched position. The latch and lock assembly also includes a first actuator configured to selectively move a locking tab between a locked position and an unlocked position. In the locked position, the locking tab is configured to block pivotable movement of the lever from the latched position to the unlatched position. In the unlocked position, the locking tab is configured to allow pivotable movement of the lever from the latched position to the unlatched position. The latch and lock assembly further includes a second actuator configured to selectively rotate a door opening tab between a first position and a second position when the locking tab is in the unlocked position. When the door opening tab is in the first position the lever is in a latched position, and when the door opening tab is rotated from the first position to the second position, the door opening tab abuts the lever and urges the lever from the latched position to the unlatched position.

Embodiments of the invention may include one or more of the following additional features separately or in combination.

In an embodiment, the locking tab may operate on a first side of the lever and the door opening tab may operate on a second side of the lever, opposing the first side of the lever.

In another embodiment, in the locked position, the locking tab may abut a portion of the lever, and in the unlocked position, the locking tab may be spaced apart from the lever.

In another embodiment, the latch and lock assembly may include a lever biasing member configured to bias the lever toward the latched position.

In another embodiment, the lever biasing member may be a spring.

In another embodiment, the first actuator and the second actuator may be pull-type solenoids.

In another embodiment, the latch and lock assembly may include a fixed housing to which at least one of the lever, first actuator, locking tab, second actuator, door opening tab and lever biasing member are mounted.

In another embodiment, the latch and lock assembly may include an adjustable housing to which the fixed housing is adjustably attached.

In another embodiment, the latch and lock assembly may include an alignment rod passing through a wall of the fixed housing and a wall of the adjustable housing to align the fixed housing relative to the adjustable housing.

In another embodiment, the latch and lock assembly may include an adjustment tuner passing through a wall of the fixed housing and a wall of the adjustable housing. The adjustment tuner may include a threaded bolt and associated jam nut, which, when tightened, prevent movement of the fixed housing relative to the adjustment housing.

In another embodiment, the latch and lock assembly may include a door opening tab adjusting block mounted to the fixed housing and including a screw. The door opening tab adjusting block may be configured to adjust the position of the door opening tab within the fixed housing relative to the lever.

In another embodiment, the latch and lock assembly may include a switch configured to detect whether and when the locking tab is in a locked position or an unlocked position.

According to another aspect of the invention, a medical device treatment machine is provided. The medical device treatment machine includes a treatment chamber for washing, disinfecting, and/or sterilizing a medical device and a door hingedly attached to the treatment chamber. The door is moveable between an open position, to expose the treatment chamber, and a closed position, to seal the treatment chamber. The door includes a latch pin on a first side of the door. The medical device treatment machine also includes a latch and lock assembly fixed to a wall of the treatment chamber. The latch and lock assembly includes a lever pivotable between a latched position and an unlatched position. In the latched position, the lever engages the latch pin to prevent movement of the door from the closed position to the open position. In the unlatched position, the lever disengages the latch pin to allow movement of the door from the closed position to the open position. The latch and lock assembly also includes a first actuator configured to selectively move a locking tab between a locked position and an unlocked position. In the locked position, the locking tab is configured to block pivotable movement of the lever from the latched position to the unlatched position. In the unlocked position, the locking tab is configured to allow pivotable movement of the lever from the latched position to the unlatched position. The latch and lock assembly also includes a second actuator configured to selectively rotate a door opening tab between a first position and a second position when the locking tab is in the unlocked position. When the door opening tab is in the first position the lever is in a latched position. When the door opening tab is rotated from the first position to the second position, the door opening tab abuts the lever and urges the lever from the latched position to the unlatched position.

Embodiments of the invention may include one or more of the following additional features separately or in combination.

In an embodiment, the medical device treatment machine may include a hinge on a second side of the door opposite the first side of the door.

In another embodiment, the hinge of the door may comprise a hinge biasing member for biasing the door toward an open position to automatically move the door from the closed position to the open position when the lever is in the unlatched position.

In another embodiment, the medical device treatment machine may include a stop pin extending from the chamber, and a stop block fixed to the door. The stop block may include a roller pin extending from the stop block in a direction configured to be perpendicular to the stop pin when the door is in a closed position. When the door is in a closed position, the roller pin may slidably abut the stop pin to permit a lateral movement of the door between the closed position and the open position and block a vertical movement of the door in a direction perpendicular to the lateral movement of the door.

In another embodiment, the medical device treatment machine may include a sensing apparatus for detecting a presence and removal of a foot of an operator in a sensing zone of the sensing apparatus. The medical device treatment machine may also include a controller for controlling the operations of the second actuator according to the detection of the presence and removal of the foot of the operator in the sensing zone of the sensing apparatus.

In another embodiment, the controller may be configured to receive a foot-presence signal from the sensing apparatus when the sensing apparatus detects the presence of the foot of the operator in the sensing zone of the sensing apparatus. The controller may also be configured to send an activation signal to an indicator apparatus on the medical device treatment machine to activate the indicator apparatus and receive a foot-removal signal from the sensing apparatus when the foot sensor detects the removal of the foot of the operator from the sensing zone of the sensing apparatus. The controller may also be configured to send an unlatch signal to the second actuator to rotate the door opening tab in abutting contact with the lever to pivot the lever from the latched position to the unlatched position.

In another embodiment, the controller may be configured to send the unlatch signal to the second actuator a predetermined period of time after receipt of the foot-removal signal.

According to another aspect of the invention, a method of operating a medical device treatment machine is provided. The method includes detecting, by a sensing apparatus disposed on the medical device treatment machine, the presence of a foot of an operator in a sensing zone of the sensing apparatus. The method also includes receiving, by a controller of the medical device treatment machine, a foot-presence signal from the sensing apparatus, and sending, by the controller, an activation signal to an indicator apparatus on the medical device treatment machine to activate the indicator apparatus. The method also includes detecting, by the sensing apparatus, the removal of the foot of the operator from the sensing zone of the sensing apparatus and receiving, by the controller, a foot-removal signal from the sensing apparatus. The method also includes sending, by the controller, an unlatch signal to an actuator of a latch and lock assembly of the medical device treatment machine and rotating, by the actuator, a door opening tab of the latch and lock assembly that is in abutting contact with a lever to pivot the lever from a latched position to an unlatched position.

Embodiments of the invention may include one or more of the following additional features separately or in combination.

In another embodiment, the unlatch signal may be sent to the actuator a predetermined period of time after receipt of the foot-removal signal.

In another embodiment, the method may include automatically moving a door of the medical device treatment machine from a closed position to an open position via a biasing force on a hinge of the door by a hinge biasing member.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

The terms "comprises" and "comprising," when used in this specification, are taken to specify the presence of stated features, integers, steps or components but do not preclude the presence or addition of one or more other features, integers, steps, components or groups thereof.

BRIEF DESCRIPTION OF THE DRAWINGS

The annexed drawings, which are not necessarily to scale, show various aspects of the present disclosure.

FIG. 8 is a flow chart of a method of operating a medical device treatment machine according to an aspect of the present invention.

DETAILED DESCRIPTION

Figures 1A, 1B:
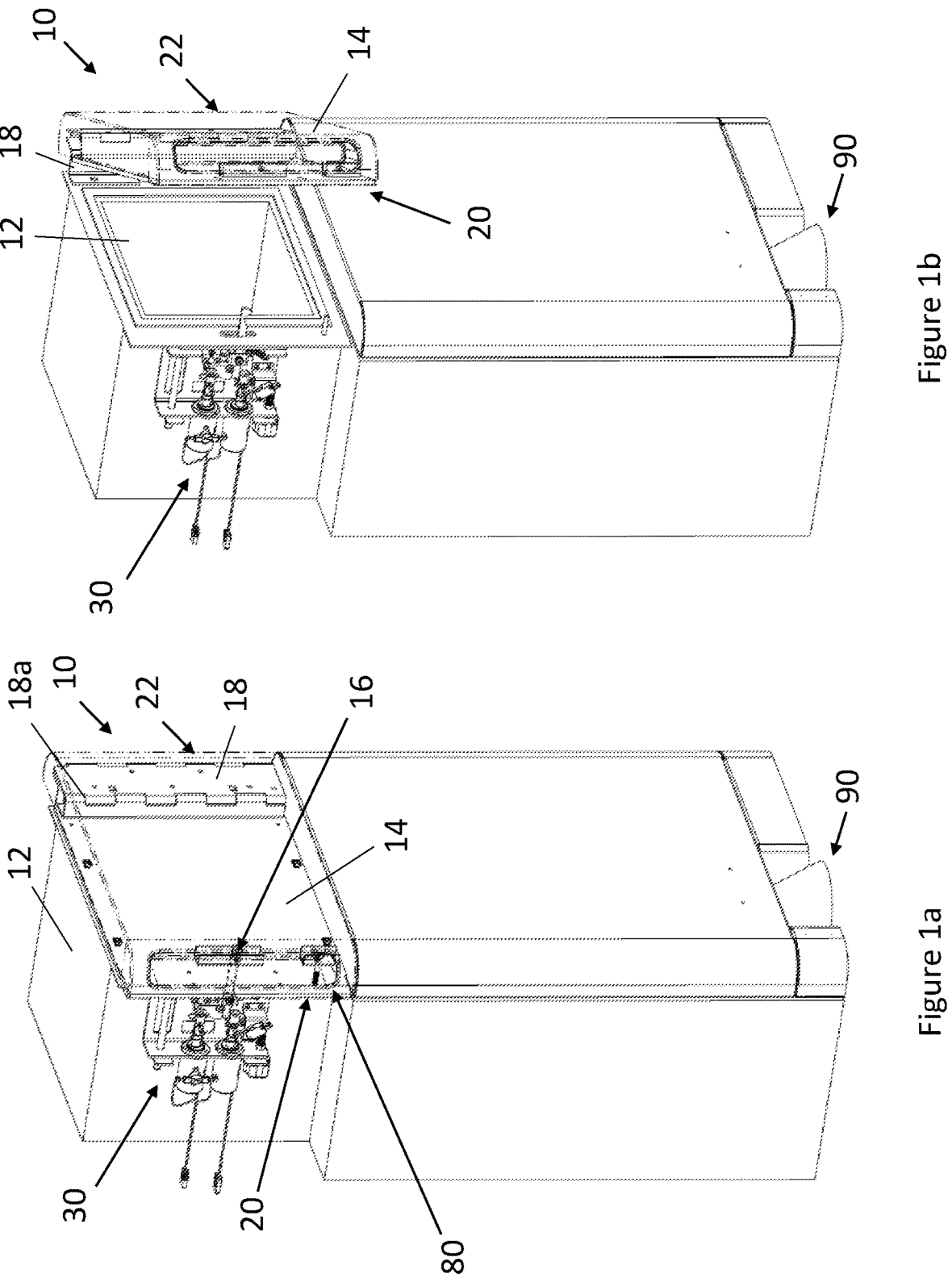
FIGS. 1a-1b are perspective views of a medical device treatment machine according to an aspect of the present invention.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

With reference to FIGS. 1a-b, a medical device treatment system, such as a medical device treatment machine 10 is generally depicted. The medical device treatment machine 10 may be, for example, a machine for washing, disinfecting and/or sterilizing a medical device, such as surgical tools or any other medical device requiring washing, disinfecting and/or sterilization before and/or after use. The medical device treatment machine 10 may include a treatment chamber 12 for washing, disinfecting and/or sterilizing the medical device. The medical device treatment machine 10 may also therefore include a door 14 hingedly attached to the treatment chamber 12. The door 14 may be automatically and/or manually moveable between a closed position, depicted in FIG. 1a, and an open position, depicted in FIG. 1b. In the closed position of the door 14, the treatment chamber 12 is closed off from the exterior of the medical device treatment machine 10 and may be sealed shut for operation of the medical device treatment machine 10. In the open position of the door 14, the treatment chamber 12 is exposed to the exterior of the medical device treatment machine 10 for insertion or removal of medical devices into or out from the treatment chamber 12.

The door 14 includes a latch pin 16 on a first side 20 of the door 14 and a hinge 18 on a second side 22 of the door 14, opposite the first side 20. A side view of the latch pin 16, wherein the door 14 is in a closed position, is shown more clearly in FIG. 5. The hinge 18 may include a hinge biasing member 18a that imparts a biasing force on the door 14 toward the open position. The door 14 may be automatically opened with the aid of the hinge biasing member 18a under certain conditions, as will later be described in detail.

Figure 5:
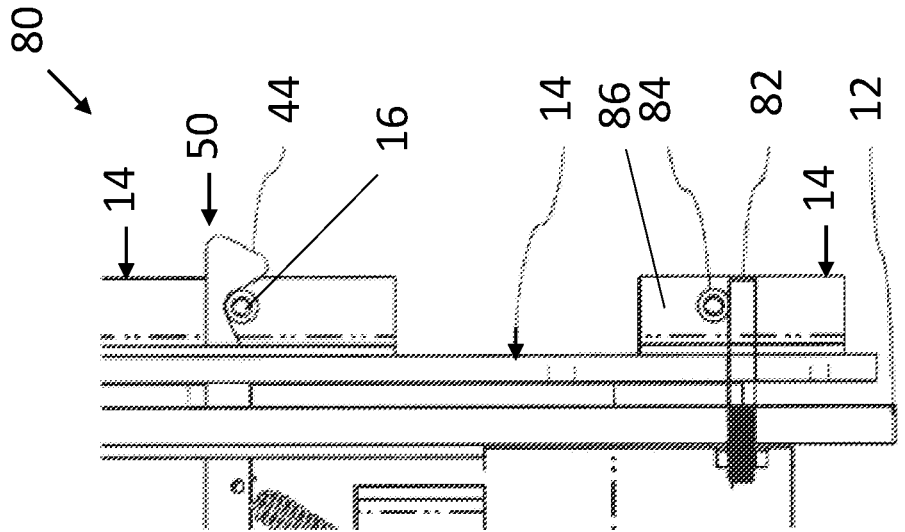
FIG. 5 is a side elevational view of a forced entry prevention mechanism on the medical device treatment machine of FIG. 1.

The medical device treatment machine 10 may include a forced entry prevention mechanism, indicated generally at 80, and a hands-free, foot-operated automatic opening mechanism, indicated generally at 90, both of which will later be described with detailed reference to FIGS. 5 and 6, respectively.

Figure 2:
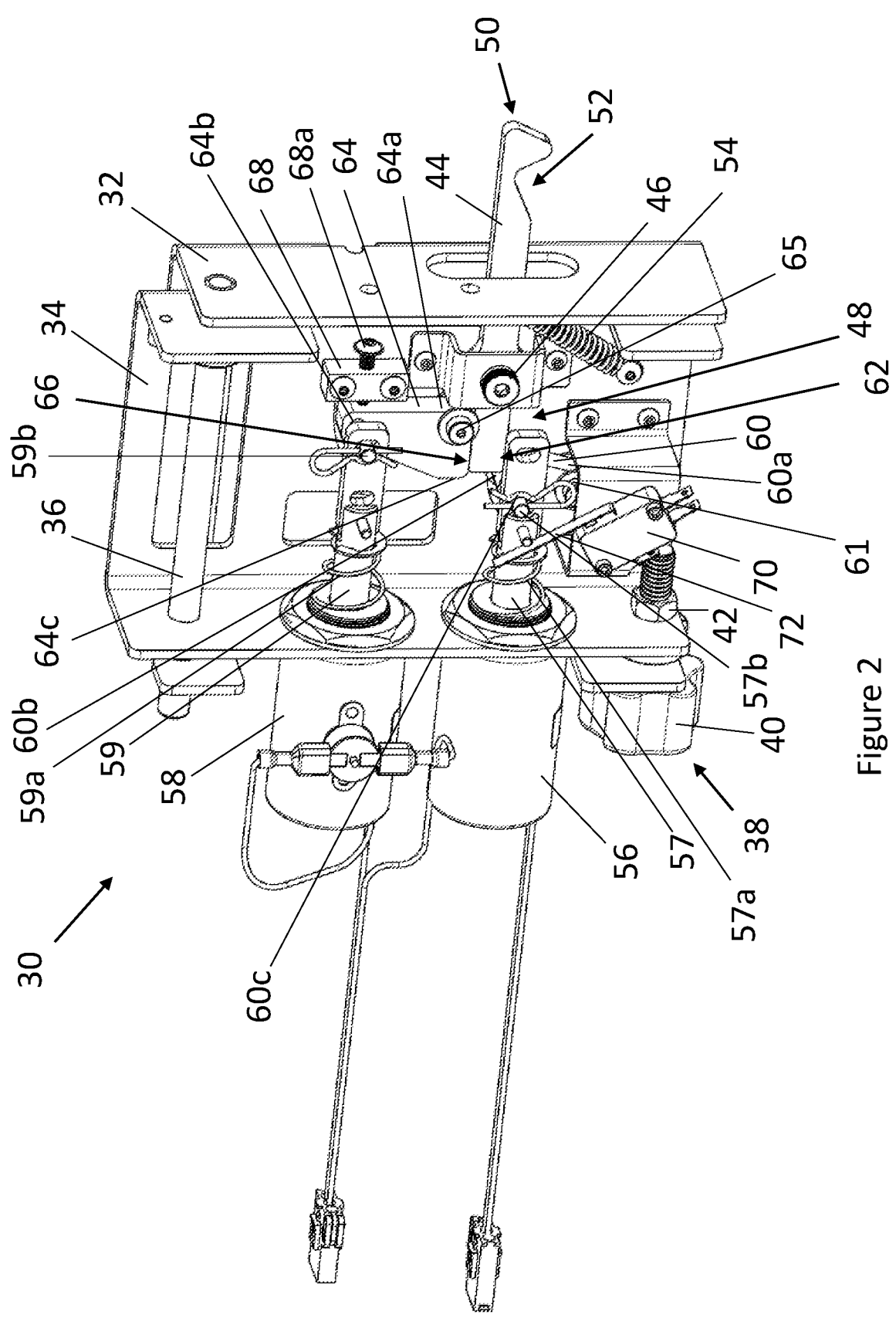
FIG. 2 is a perspective view of a latch and lock assembly of the medical device treatment machine of FIG. 1, shown in a latched and locked state.
Figure 3:
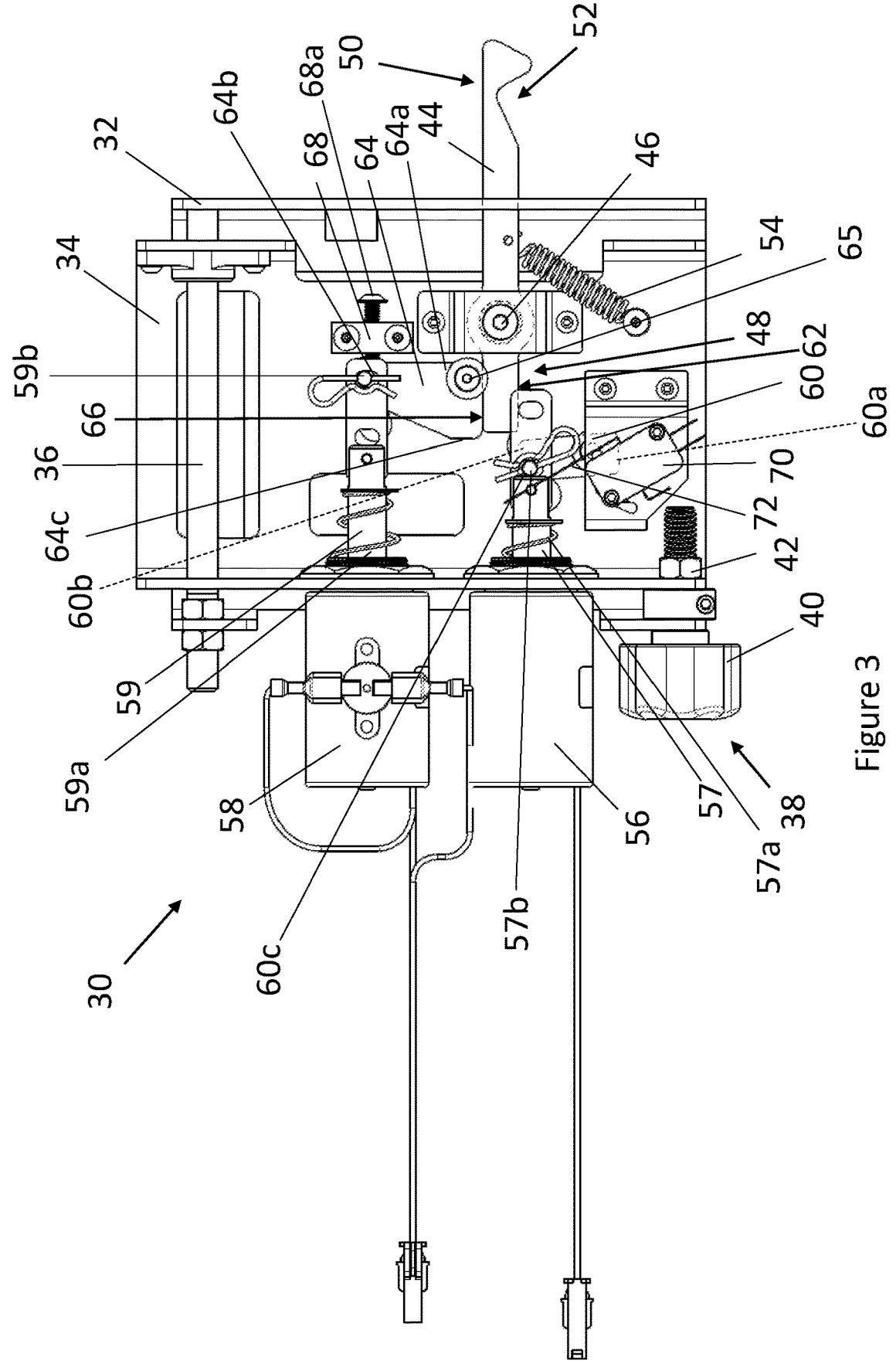
FIG. 3 is a side elevational view of the latch and lock assembly of FIG. 2, shown in an unlocked and latched state.
Figure 4:
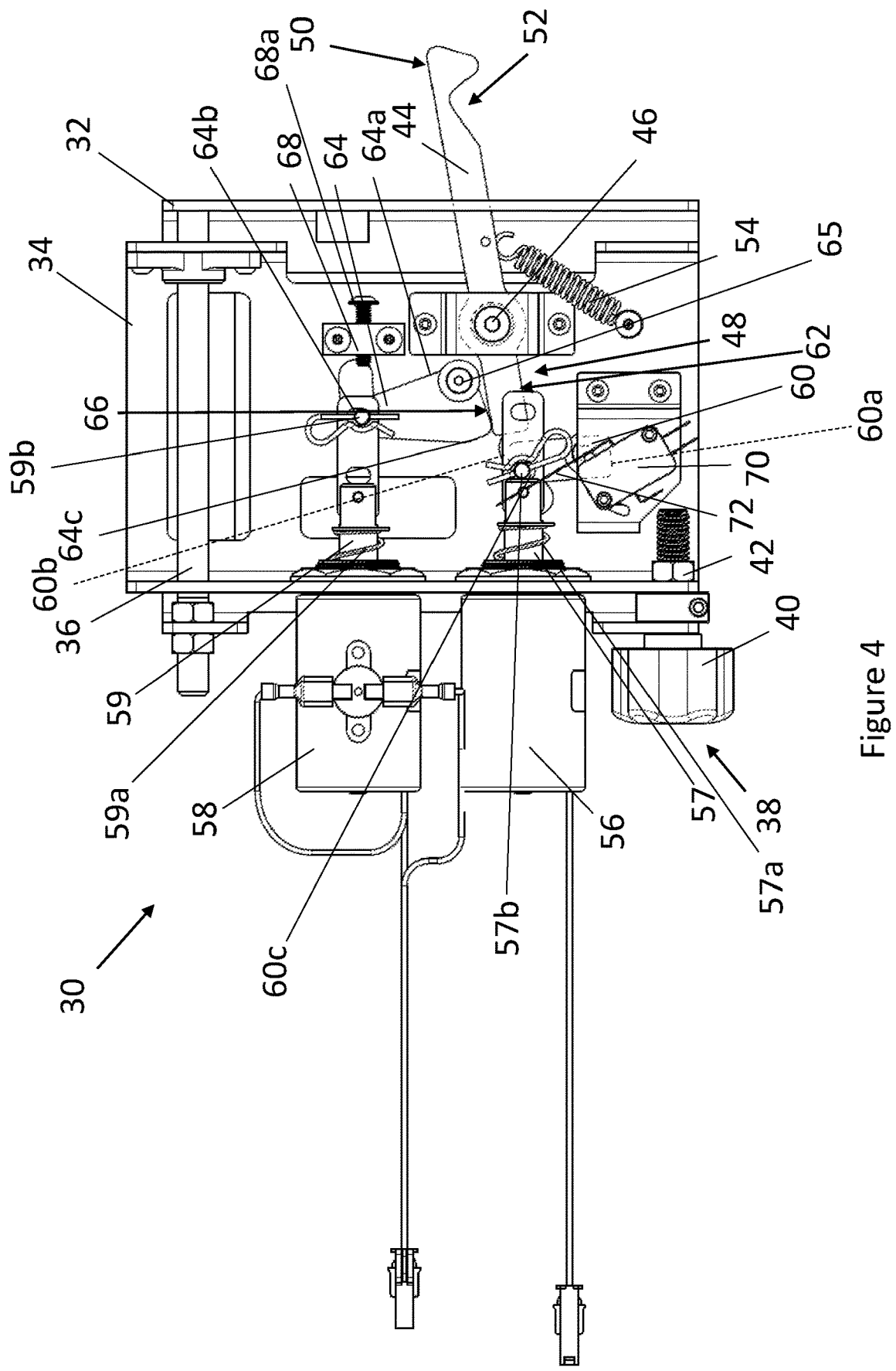
FIG. 4 is a side elevational view of the latch and lock assembly of FIG. 2, shown in an unlocked and unlatched state.

With reference to FIGS. 2-4, the medical device treatment machine 10 includes a latch and lock assembly 30 for latching/unlatching and locking/unlocking the door 14. The latch and lock assembly 30 may be mounted to a side wall of the treatment chamber 12 associated with the first side 20 of the door 14 having the latch pin 16, as shown, or otherwise disposed between the latch pin 16 of the door 14 and the treatment chamber 12 of the medical device treatment machine 10.

FIGS. 2-4 depict the components of the latch and lock assembly 30 in further detail. As depicted, the latch and lock assembly 30 includes an adjustment assembly 32 and a fixed assembly 34, adjustably connected to each other with an alignment rod 36 and an adjustment tuner 38. The adjustment assembly 32 may be installed directly onto the side wall of the treatment chamber 12, while the fixed assembly 34 may be arranged within the boundaries of, and adjustably mounted to, the adjustment assembly 32. Various other components of the latch and lock assembly 30 may therefore be mounted to and/or disposed within the boundaries of the fixed assembly 34. In the illustrative embodiment, the adjustment assembly 32 and the fixed assembly 34 are adjustably connected relative to one another by the alignment rod 36 at an upper end and the adjustment tuner 38 at the lower end. The alignment rod 36 and the adjustment tuner 38 provide adjustability to the latch and lock assembly 30 to account for any manufacturing tolerances involved in the latch and lock assembly 30 or its integration/installation into the medical device treatment machine 10.

The alignment rod 36 may be a cylindrical rod that aligns the fixed assembly 34 relative to the adjustment assembly 32 and allows for fast and simple adjustment and movement of the fixed assembly 34 to accommodate for any manufacturing tolerances or desired adjustments for a particular application. As illustrated, the alignment rod 36 passes through at least one wall of the fixed assembly 34 and at least one wall of the adjustment assembly 32 and the adjustment tuner 38 similarly passes through at least one wall of the fixed assembly 34 and at least one wall of the adjustment assembly 32. The adjustment tuner 38 may include a threaded bolt 40 having an associated jam nut 42 configured to move the fixed assembly 34 linearly inwards or outwards relative to the adjustment assembly 32 (to the right and left in FIGS. 2-4). The alignment rod 36 ensures proper linear alignment when the fixed assembly 34 is moved relative to the adjustment assembly 32. The associated jam nut 42, when tightened down after adjustment, prevents rotation of the adjustment tuner 38 and therefore secures the position of the fixed assembly 34 and any of the components within and/or mounted to the fixed assembly 34 relative to the adjustment assembly 32, to prevent any undesired relative movement or adjustment. The alignment rod 36 and adjustment tuner 38 may therefore provide both adjustability to and security of the position of the latch and lock assembly 30 throughout its entire service life.

The latch and lock assembly 30 includes a lever 44 pivotably fixed to the fixed assembly 34 by means of a pivot fastener 46 (or other pivot means including a pivot pin, hinge, or bearing, among others), with an actuation end 48 of the lever 44 on one side of the pivot fastener 46 and a latching end 50 of the lever 44 on the opposite side of the pivot fastener 46. The lever 44 is pivotable about its pivot fastener 46 between a latched position, depicted in FIGS. 2 and 3, and an unlatched position, depicted in FIG. 4. The lever 44 includes an open-hook recess 52 near or at an end of the latching end 50 of the lever 44 that engages the latch pin 16 of the door 14 when the door 14 is in the closed position and the lever 44 is in the latched position, as shown for example in FIG. 5. The fixed assembly 34 and adjustment assembly 32 include openings through which the lever 44 extends, such that the open hook recess 52 portion of the lever 44 extends to and is therefore engageable with the latch pin 16 of the door 14 when the door 14 is in a closed position. The latch and lock assembly 30 may also include a lever biasing member 54 attached to the fixed assembly 34 and lever 44 in a manner to bias the lever 44 toward the latched position. In an embodiment, the lever biasing member 54 may be a tension spring, as shown, or any other type of biasing means.

The illustrated latch and lock assembly 30 has a dual actuator configuration, comprising a first actuator 56 and a second actuator 58 that selectively and cooperatively control the position of the lever 44 of the latch and lock assembly 30. The first actuator 56 and second actuator 58 may be, for example, solenoids. In the illustrative embodiment, the first actuator 56 and the second actuator 58 are pull-type solenoids, wherein in their unactuated state, their respective actuation rods 57 and 59 are extended due to a spring force exerted by respective springs 57*a* and 59*a* of the actuators 56 and 58, and when actuated, their actuation rods 57 and 59 are retracted against the spring force of the springs 57*a* and 59*a*, thereby retracting the respective actuation rods 57 and 59 and thus pulling the components to which the actuation rods 57 and 59 are respectively connected. In other embodiments, push-type solenoids and/or other suitable actuators are contemplated. In this regard, the actuators may be driven electrically and/or pneumatically, for example, and may have any suitable arrangement including for example in-line, as shown, belt driven or gear driven, among others.

The first actuator 56 selectively moves a locking tab 60 by rotatable connection to the locking tab 60. The locking tab 60 has a pivot end 60*a* at one end, an abutment end 60*b* at an opposite end, and a coupling aperture 60*c* therebetween. The pivot end 60*a* is rotatably mounted to the fixed assembly 34 via a pivot fastener 61 (or other pivot means including a pivot pin, hinge, or bearing, among others). The actuation rod 57 of the first actuator 56 is rotatably coupled to the locking tab 60 at the coupling aperture 60*c* via a pin 57*b*.

Extension and retraction of the actuation rod 57 is linear and the coupling aperture 60*c* may be configured as a vertical slot to compensate for linear movement of the actuation rod 57. Extension of the actuation rod 57, as by spring biasing force, translates into clockwise pivotable movement of the locking tab 60 about the pivot fastener 61, which, in turn, urges the abutment end 60*b* of the locking tab 60 into an abutment position relative to, in the illustrative embodiment below, a first side 62 (lower side, as shown) of the actuation end 48 of the lever 44. Retraction of the actuation rod 57, as by energization of the actuator 56 overcoming the force exerted by spring 57*a*, translates into counterclockwise pivotable movement of the locking tab 60 about the pivot fastener 61, which, in turn, urges the abutment end 60*b* of the locking tab 60 out of an abutment position relative to, in the illustrative embodiment out from below, the first side 62 of the actuation end 48 of the lever 44.

The first actuator 56 is thus configured to selectively rotate, or move, the locking tab 60 between a locked position, depicted in FIG. 2, and an unlocked position, depicted in FIGS. 3 and 4. Specifically, in the locked position, the locking tab 60 is positioned directly next to the lever 44 on the first side 62 of the lever 44, in abutting contact with at least a portion of the lever 44 at the actuation end 48 of the lever 44. In the locked position, therefore, the abutment end 60*b* of the locking tab 60 obstructs the path of movement of the actuation end 48 of the lever 44, and thus physically blocks pivotable movement of the lever 44 from the lever's latched position to the lever's unlatched position. In the unlocked position, however, the abutment end 60*b* of the locking tab 60 does not obstruct the path of movement of the actuation end 48 of the lever 44, and instead is spaced wholly apart from the lever 44, that is out of the way of the actuation end 48 of the lever 44, thereby allowing pivotable movement of the lever 44 from the lever's latched position to the lever's unlatched position.

The second actuator 58 selectively moves a door opening tab 64 by rotatable connection to the door opening tab 64. In the illustrative embodiment, the door opening tab 64 takes the form of a cam, it being appreciated that other forms are possible and contemplated herein. The door opening tab 64 has a pivot end 64*a* at one end, a coupling aperture 64*b* at an opposite end, and a cam segment 64*c* laterally offset from the pivot end 64*a* and the coupling aperture 64*b*, in the illustrative embodiment laterally offset from a line connecting the pivot end 64*a* and the coupling aperture 64*b*. In the illustrative embodiment, the door opening tab 64 has an L-shape configuration with the coupling aperture 64*b* at the end of one leg of the L, the cam segment 64*c* at the end of the other leg of the L, and the pivot end 64*a* at the junction of the legs of the L. The pivot end 64*a* is rotatably mounted to the fixed assembly 34 via a pivot fastener 65 (or other pivot means including a pivot pin, hinge, or bearing, among others). The actuation rod 59 of the second actuator 58 is rotatably coupled to the door opening tab 64 at the coupling aperture 64*b* via a pin 59*b*. Extension and retraction of the actuation rod 59 is linear and the coupling aperture 64*b* may be configured as a vertical slot to compensate for linear movement of the actuation rod 59. Extension of the actuation rod 59, as by spring biasing force, translates into clockwise pivotable movement of the door opening tab 64 about the pivot fastener 65, which, in turn, urges the cam segment 64*c* of the door opening tab 64 into a first adjacent position relative to, in the illustrative embodiment above, a second side 66 of the actuation end 48 of the lever 44. In the first adjacent position, which may also be referred to as a locking enable position or a latching enable position, the cam segment 64c of the door opening tab 64 enables the lever 44 to be rotated clockwise about the pivot fastener 46, as by the lever biasing member 54, such that the first side 62 of the actuation end 48 of the lever 44 is in an out of the way position to enable the locking tab 60 to be rotated clockwise to a position in which the abutment end 60b thereof is underneath the first side 62 thereby obstructing the path of movement of the actuation end 48 and locking the lever 44 into the latched position.

When the cam segment 64c of the door opening tab 64 is in the first adjacent position, the second side 66, i.e. upper side in the illustrative embodiment, of the actuation end 48 of the lever 44 may abut the cam segment 64c, as shown, although this need not be the case and other embodiments are contemplated. In an embodiment, when the cam segment 64c of the door opening tab 64 is in the first adjacent position, the second side 66 of the actuation end 48 of the lever 44 may abut a structure other than the cam segment 64c, so long as the lever 44 is in an out of the way position to enable the locking tab 60 to be rotated to a locked position. For example, when the cam segment 64c of the door opening tab 64 is in the first adjacent position, the second side 66 of the actuation end 48 of the lever 44 may abut the coupling aperture 64b end of the door opening tab 64 or a stop member attached to or formed as part of the fixed assembly 34. It will further be appreciated that when the cam segment 64c of the door opening tab 64 is in the first adjacent position, any portion of the lever 44, not necessarily the second side 66 of the actuation end 48, may abut any other structure of the latch and lock assembly 30 to resist clockwise movement of the lever 44 about the pivot fastener 46 and thus position the lever 44 out of the path of movement of the locking tab 60 so that locking can occur. For example, the central portion of the lever surrounding the pivot fastener 46 may be equipped with a radially projecting protuberance that abuts a stop member in of the latch and lock assembly 30 to resist such clockwise movement.

Reference is again made to FIG. 3, which shows the latch and lock assembly 30 in an unlocked state, more specifically the abutment end 60b of the locking tab 60 has been moved out of the way from the actuation end 48 of the lever 44, that is, not obstructing the path of movement of the actuation end 48 of the lever 44. With the latch and lock assembly 30 in the unlocked state, retraction of the actuation rod 59, as by energization of the actuator 58 overcoming the force exerted by spring 59a (and the lever biasing member 54), translates into counterclockwise pivotable movement of the door opening tab 64 about the pivot fastener, which, in turn, urges the cam segment 64c of the door opening tab 64 into a second adjacent position relative to, in the illustrative embodiment above, the second side 66 of the actuation end 48 of the lever 44. The cam segment 64c of the door opening tab 64 is lower in the second adjacent position, which is shown in FIG. 4, than in the first adjacent position, which is shown in FIG. 3. In the second adjacent position, which may also be referred to as an unlatching position, the cam segment 64c of the door opening tab 64 abuts the second side 66, in the illustrative embodiment the upper side, of the actuation end 48 of the lever 44, and urges the lever 44 counterclockwise about the pivot fastener 46, as by energization force of the actuator 58 overcoming the biasing force of the lever biasing member 54 (and the force exerted by the spring 59a), such that the open hook recess 52 near or at the latching end 50 of the lever 44 is sufficiently raised and out of the way to enable withdrawal of the latch pin 16 of the door 14, that is, to enable opening of the door 14 (automatically or manually).

The second actuator 58 thus selectively rotates the door opening tab 64 between a first position, depicted in FIGS. 2 and 3, and a second position, depicted in FIG. 4. The rotation of the door opening tab 64 by the second actuator 58, however, is limited by the position of the locking tab 60, described elsewhere herein. Specifically, the second actuator 58 is configured to rotate the door opening tab 64 from the first position to the second position when the locking tab 60 is in the unlocked position, that is, when the locking tab 60 is not obstructing the path of movement of the actuation end 48 of the lever 44.

In the illustrative embodiment, in both the first position and the second position, the door opening tab 64 is positioned next to the actuation end 48 of the lever 44 on the second side 66 of the lever 44. In the first position, the door opening tab 64 may be in abutting contact with at least a portion of the lever 44 at the actuation end 48 of the lever 44, although this need not be the case, as described above. As the door opening tab 64 is rotated from the first position to the second position, the door opening tab 64 abuts at least a portion of the lever 44, for example at the second side 66 of the actuation end 48 thereof, to urge movement of the lever 44 about the pivot fastener 46. The cam segment 64c and more generally the door opening tab 64 may have a triangular or oblong shape, such that rotational movement of the door opening tab 64 from the first position to the second position imparts a downward force on the lever 44 (as viewed in FIGS. 2-4). The downward force imparted on the lever 44 by the rotation of the door opening tab 64 overcomes the biasing force of the lever biasing member 54 and therefore pivots the lever 44 from the latched position to the unlatched position and disengages the open hook recess 52 of the lever 44 from the latch pin 16 of the door 14. Rotational movement of the door opening tab 64 from the second position to the first position relieves the overcoming downward force on the lever 44, thereby allowing the lever 44 to pivot from the unlatched position to the latched position due to the biasing force of the lever biasing member 54.

The position and arrangement of the first actuator 56 and the second actuator 58 in relation to each other and other components in relation to the actuators 56, 58 reduce the overall size of the latch and lock assembly 30 and help keep all components substantially in the same plane for easy access. Referring to FIG. 2, for example, the first and second actuators 56, 58 are positioned adjacent one another and lie in the same actuator plane, and their respective rods 57, 59 likewise actuate in the same plane. The lever 44, the locking tab 60, and the door opening tab 64 are adjacent one another and lie in the same locking/latching plane. As is also shown in FIG. 2, the actuator plane is laterally adjacent and parallel to the locking/latching plane, which adds to the accessibility and compactness of the design. The pivot fasteners 46, 61, 65, and pivot pins 57b, 59b, having their respective pivot axes transverse, perpendicular in the illustrative embodiment, to the respective actuator plane and locking/latching plane.

The latch and lock assembly 30 may include a door opening tab adjusting block 68 fixed to the fixed assembly 34 and configured to allow adjustment of the position of the door opening tab 64. Adjustment of the position of the door opening tab 64 in the first position may affect the vertical position of the lever 44 for example in embodiments where the door opening tab 64 in the first position is in abutting relation with the lever 44, for example as shown in FIGS. 2 and 3. The door opening tab adjusting block 68 may also therefore be configured to allow adjustment of the vertical position of the lever 44 to ensure complete engagement between the open hook recess 52 on the lever 44 and the latch pin 16 of the door 14 when the door 14 is in the closed position and the lever 44 is in the latched position. In the illustrative embodiment, the door opening tab adjusting block 68 includes a tapped block having a screw 68*a* threaded therein that abuts the door opening tab 64 and when rotated adjusts the position of the door opening tab 64 relative to the lever 44.

The latch and lock assembly 30 may also include a switch 70 that is electrically connected to a controller of the medical device treatment machine 10 for signaling to the controller when the latch and lock assembly 30 is in a locked or unlocked state. The switch 70 may be fixed to the fixed assembly 34 and may include an extending arm 72 that is actuated when the first actuator 56 moves the locking tab 60 from the locked position to the unlocked position. When the latch and lock assembly 30 is in an unlocked state (i.e., when the locking tab 60 is in the unlocked or non-obstructing position), the extending arm 72 of the switch 70 is actuated and the switch 70 is configured to send an unlocked signal to the controller, signaling the unlocked state. When the latch and lock assembly 30 is in a locked state (i.e., when the locking tab 60 is in the locked or obstructing position), the extending arm 72 of the switch 70 is not actuated and the switch 70 is configured to send a locked signal to the controller, signaling the locked state. In this way, the controller of the medical device treatment machine 10 actively senses whether and when the latch and lock assembly 30 is in the locked or unlocked state at any given moment.

The latch and lock assembly 30 may therefore be in any one of: a) a locked/latched state, depicted in FIG. 2, wherein the latch and lock assembly 30 holds the door 14 in the closed position and does not allow the door 14 to be manually or automatically moved to the open position, b) an unlocked/latched state, depicted in FIG. 3, wherein the latch and lock assembly 30 holds the door 14 in the closed position and allows the door 14 to be manually moved to the open position for example, by manually opening the door 14 to urge the lever 44 upward (counter clockwise in FIGS. 3 and 4) against the biasing force of the lever biasing member 54, or c) an unlocked/unlatched state, depicted in FIG. 4, wherein the latch and lock assembly 30 does not hold the door 14 in the closed position and therefore allows the door 14 to be manually and/or automatically moved to the opened position. Which state the latch and lock assembly 30 is in at any given moment is determined by the operation of the first actuator 56 and the second actuator 58 and, therefore, the position of the lever 44 as limited and affected by the position and movement of the locking tab 60 and door opening tab 64.

The locked/latched state, depicted in FIG. 2, is the default state of the latch and lock assembly 30, where neither the first actuator 56 nor the second actuator 58 are energized. Accordingly, in the event of a power or system shut-off during a treatment cycle of the medical device treatment machine 10, when the door 14 is in a closed position and the latch and lock assembly 30 is in the locked/latched state, the latch and lock assembly 30 will remain in the locked/latched state. In the locked/latched state, the lever 44 of the latch and lock assembly 30 is in the latched position, engaging the latch pin 16 of the door 14. The locking tab 60 is in the locked position, obstructing the path of movement of the actuation end 48 of the lever 44, and blocking the lever 44 from becoming unlatched (blocking the lever 44 from moving from the latched position to the unlatched position). The door opening tab 64 is in the first position, imparting no force (if not in abutting contact with the lever 44) or a minimal amount of force (if in abutting contact with the lever 44) on the actuation end 48 of the lever 44. Accordingly, the lever 44 is maintained in the latched position by the biasing force of the lever biasing member 54 and the blocking of pivotable movement of the lever 44 by the locking tab 60. Accordingly, in the locked/latched state of FIG. 2, it is ensured that the door 14 of the medical device treatment machine 10 remains closed and locked and the door 14 is neither manually nor automatically moveable from the closed position to the open position.

Upon activation of the first actuator 56, the latch and lock assembly 30 transitions to the unlocked/latched state, depicted in FIG. 3. In the unlocked/latched state, the locking tab 60 is in the unlocked position such that the abutment end 60*b* of the locking tab 60 does not obstruct the path of movement of the actuation end 48 of the lever 44, and instead is spaced wholly apart from the lever 44, as moved by the first actuator 56. The locking tab 60, therefore, no longer blocks pivotable movement of the lever 44 from the latched position to the unlatched position. Accordingly, although the lever 44 is maintained in the latched position by the biasing force of the lever biasing member 54 on the lever 44, clockwise in the illustrative embodiment, the biasing force of the lever biasing member 54 may be overcome by manual force and/or automatic force. For example, manual operation of a door handle, pulling the door 14 and thus the latch pin 16 away from the treatment chamber 12, or the like, may impart an overcoming force on the lever 44, opposite that of the biasing force of the lever biasing member 54, counterclockwise in the illustrative embodiment, thereby pivoting the lever 44 from the latched position to the unlatched position. For example, referring to FIG. 5, pulling the door 14 will urge the latch pin 16 rightward against a declining portion of the open hook recess 52, thus urging the latching end 50 of the lever 44 upward, and the lever 44 itself counterclockwise, thereby unlatching the lever 44 from the latch pin 16. In the unlocked/latched state, therefore, the door 14 may be manually moved from the closed position to the open position upon manually pivoting of the lever 44 from the latched position to the unlatched position.

Automatic, hands-free movement of the door 14 from the closed position to the open position, however, may be achieved upon actuation of the second actuator 58. Upon activation of the second actuator 58, the latch and lock assembly 30 transitions to the unlocked/unlatched state. In the unlocked/unlatched state, the door opening tab 64 is in the second position, as rotated by the second actuator 58. The door opening tab 64, therefore, imparts a downward force on the actuation end 48 and the second side 66 of the lever 44, countering and overcoming the biasing force of the lever biasing member 54 (and the spring force of the spring 59*a*). The lever 44 is therefore pivoted to the unlatched position and disengages the latch pin 16 of the door 14. The door 14 is then free to automatically move to the open position due to for example stored potential energy, gravity, spring or elastic forces or otherwise. For example, the hinge biasing member of the hinge 18 may automatically push the door 14 to an open position with its stored potential energy. The hinge 18 may be configured to automatically push the door 14 to an open position that is only a few inches open, such that an operator may manually move the door 14 to a more open position.

Other features of the medical device treatment machine 10 will now be described. With reference to FIG. 5, the medical device treatment machine 10 may include a forced-entry prevention mechanism 80. The forced-entry prevention mechanism 80 is integrated into the medical device treatment machine 10 between the treatment chamber 12 and the door 14 to ensure that an operator cannot use excessive physical force to open the door 14 of the medical device treatment machine 10 when the door 14 is in the closed position and the latch and lock assembly 30 is in a latched and locked state. The forced-entry prevention mechanism 80 includes a stop pin 82 fixed to the treatment chamber 12 that projects outward from the treatment chamber 12 into the vicinity of the door 14 of the medical device treatment machine 10. The forced-entry prevention mechanism 80 also includes a roller pin 84 fixed to the door 14 in a position aligned for abutting engagement with the stop pin 82 of the treatment chamber 12 when the door 14 is in the closed position. In the illustrative embodiment, for example in FIG. 5, the roller pin 84 is positioned for perpendicular alignment with the stop pin 82 when the door 14 is in the closed position.

The stop pin 82 may be a smooth projection and the roller pin 84 may be a free-rotating cylindrical roller. In an embodiment, the roller pin 84 may extend from a stop block 86 that is fixed to the door 14. The roller pin 84 is positioned to engage the stop pin 82 on a side of the stop pin 82 that is proximal to the latch and lock assembly 30 (the upper side of the stop pin 82 in the FIG. 5 embodiment) such that when the door 14 is in the closed position, the engagement of the roller pin 84 and the stop pin 82 provides an opposing point of contact between the door 14 and the treatment chamber 12. This provides resisting mitigation to downward force that may otherwise overcome the biasing force of the lever biasing member 54 and the locking tab 60 that maintain the latch and lock assembly 30 in the latched and locked state.

Accordingly, the roller pin 84 is configured to slidably abut the stop pin 82 to permit pivotable movement of the door 14 between the closed position and the open position but block a vertical movement of the door 14 in a direction perpendicular to the plane of pivotable movement of the door 14 when the door 14 is in the closed position. This effectively prevents a forced opening of the door 14 when the latch and lock assembly 30 is in a latched and locked state. In FIG. 5, for example, attempts to force the door 14 downward and/or the latching end 50 of the lever 44 upward to withdraw the latch pin 16 from the open hook recess 52 of the lever 44, which would allow the door 14 to be opened, are prevented or at least significantly impeded by the roller pin 84 abutting the stop pin 82. It will be appreciated, of course, that a forced-entry prevention mechanism could also, or alternatively, be positioned vertically above (in FIG. 5) the latch and lock assembly 30, which forced-entry prevention mechanism would provide resisting mitigation to upward force that may otherwise overcome the biasing force of the lever biasing member 54 and the locking tab 60 that maintain the latch and lock assembly 30 in the latched and locked state. On the other hand, because the stop pin 82 is smooth and the roller pin 84 is free-rotating, no additional stored potential energy is required to open the door 14 automatically when the latch and lock assembly 30 is in the unlocked/unlatched position.

Figure 6:
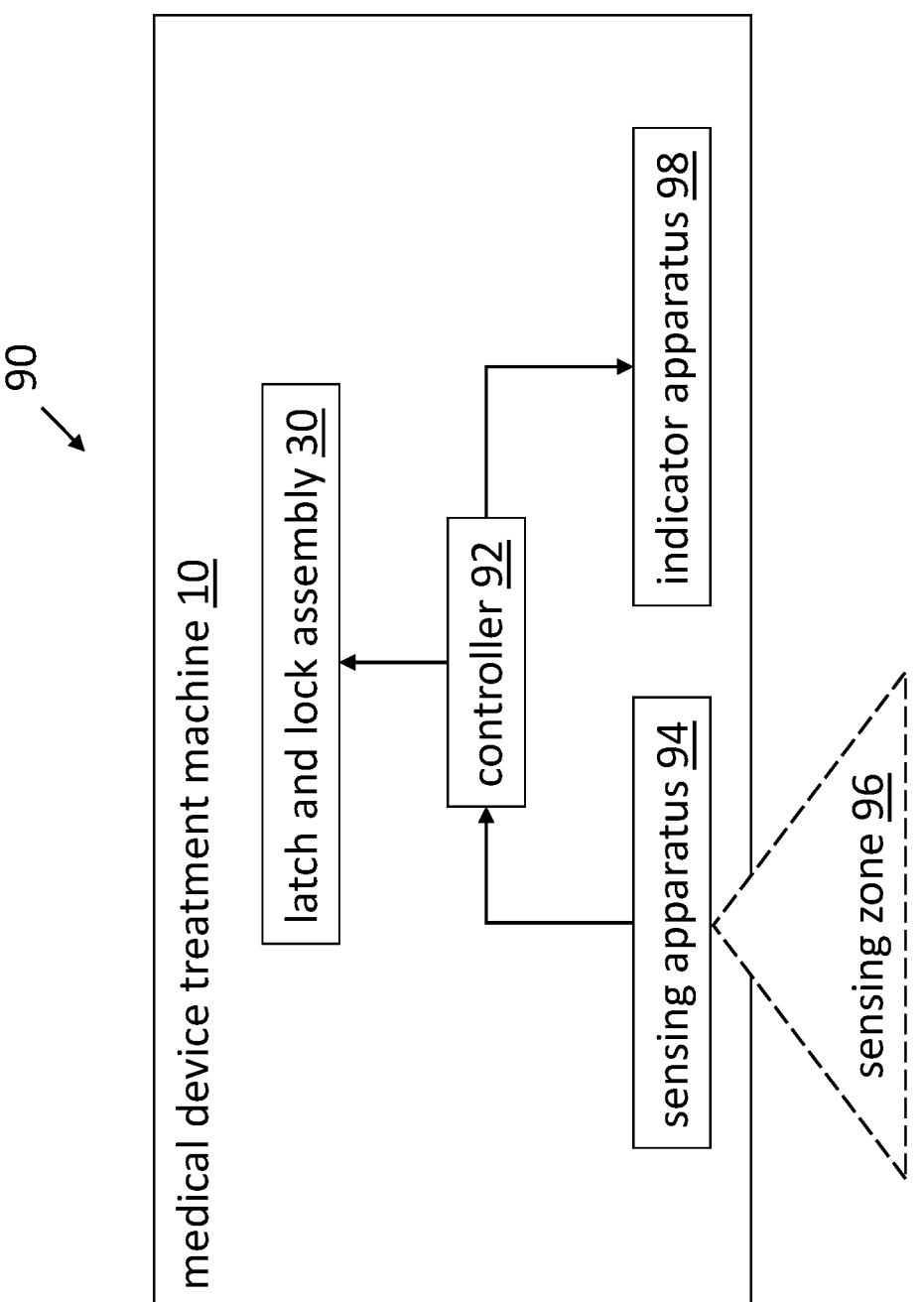
FIG. 6 is a schematic diagram of a foot-operated automatic opening mechanism of the medical device treatment machine of FIG. 1.

With reference to FIG. 6, the medical device treatment machine 10 may include a foot-operated automatic door opening mechanism 90. In an embodiment, the foot-operated automatic door opening mechanism 90 may be activated when the latch and lock assembly 30 is in the unlocked/latched state. In this embodiment, the operator may either manually transition the latch and lock assembly 30 from the unlocked/latched state to the unlocked/unlatched state to open the door 14, or may initiate automatic transitioning of the latch and lock assembly 30 to the unlocked/unlatched state and automatic opening of the door 14 by use of the foot-operated automatic door opening mechanism 90. In another embodiment, the foot-operated automatic door opening mechanism 90 may be activated when the latch and lock assembly 30 is in the locked/latched state. In this embodiment, the operator may use the foot-operated automatic door opening mechanism 90 to both automatically transition the latch and lock assembly 30 from the locked/latched state to the unlocked/latched state and automatically transition the latch and lock assembly 30 from the unlocked/latched state to the unlocked/unlatched state to open the door 14.

The foot-operated automatic door opening mechanism 90 includes a sensing apparatus 94 and an indicator apparatus 98. The sensing apparatus 94 and the indicator apparatus 98 are configured to interface with each other, and with the latch and lock assembly 30, via a controller 92 that is configured to control the operations, and timing of the operations, of the first actuator 56 and/or the second actuator 58 of the latch and lock assembly 30.

In an embodiment, the sensing apparatus 94 is a proximity sensor configured to detect the presence and removal of a foot of an operator in a sensing zone 96 of the sensing apparatus 94. In another embodiment, the sensing apparatus 94 may be a pedal or lever disposed in the sensing zone 96 and configured to be engaged and disengaged by a foot of an operator, which engagement and disengagement respectively provide an indication of the presence and removal of the foot of the operator in the sensing zone 96 of the sensing apparatus 94. The sensing apparatus 94 may be disposed near a bottom of the medical device treatment machine 10 such that the sensing zone 96 of the sensing apparatus 94, within which the sensing apparatus 94 may detect the presence and removal of the foot of the operator, is near the ground where the medical device treatment machine 10 rests. When the operator wishes to initiate the automatic opening of the door 14 of the medical device treatment machine 10, the operator may activate the sensing apparatus 94 by positioning his or her foot in the sensing zone 96 of the sensing apparatus 94, for example by waving the foot within the sensing field of the proximity sensor in one embodiment, or by moving the pedal or lever with the foot in the other embodiment, and may deactivate the sensing apparatus 94 by removing his or her foot from the sensing zone 96 of the sensing apparatus 94 for example, by moving the foot out of the sensing field of the proximity sensor in one embodiment, or by removing the foot from the pedal or lever in the other embodiment. The sensing apparatus 94 is therefore configured to detect the presence and removal of the foot of the operator in the sensing zone 96 of the sensing apparatus 94 where the detection is by means of a sensing field of a proximity sensor or engagement and disengagement of a lever or pedal.

The controller 92 is configured to control the first actuator 56 and/or the second actuator 58 of the latch and lock assembly 30 according to the detection of the presence and removal of the foot of the operator in the sensing zone 96 of the sensing apparatus 94. In an embodiment, the controller 92 is configured to receive a foot-presence signal from the sensing apparatus 94 when the sensing apparatus 94 detects the presence of the foot of the operator in the sensing zone 96 of the sensing apparatus 94 for example, by detection of the foot in the sensing field of a proximity sensor or by detection of movement of a pedal or lever.

Upon receipt of the foot-presence signal, the controller 92 is configured to send an activation signal to the indicator apparatus 98 of the medical device treatment machine 10 to activate the indicator apparatus 98. In one form, the indicator apparatus 98 may include a light indicator that either illuminates or changes color when activated. In another form, the indicator apparatus 98 may include an audible sound. The indicator apparatus 98 may be positioned anywhere on the medical device treatment machine 10 such that it is detectable (visible and/or audible) to the operator. The activation of the indicator apparatus 98, such as the illumination or change of color of the light indicator, provides a visual (or audible) feedback to the operator that the sensing apparatus 94 has been activated and that the operator may remove their foot from the sensing zone 96 of the sensing apparatus 94. The controller 92 is configured to receive a foot-removal signal from the sensing apparatus 94 when the sensing apparatus 94 detects the removal of the foot of the operator from the sensing zone 96 of the sensing apparatus 94 for example, by detection that the foot is outside the sensing field of the proximity sensor or by detection that the foot has been removed from the pedal or lever.

Upon receipt of the foot-removal signal, the controller 92 is then configured to control the operations, and the timing of the operations, of the first actuator 56 and/or the second actuator 58 of the latch and lock assembly 30. In the embodiment in which the foot-operated automatic door opening mechanism 90 is activated when the latch and lock assembly 30 is in the unlocked/latched state, upon receipt of the foot-removal signal, the controller 92 is configured to send an unlatch signal to the second actuator 58 to rotate the door opening tab 60 to pivot the lever 44 from the latched position to the unlatched position after a predetermined period of time from receipt of the foot removal signal. The predetermined period of time may be configured by the controller 92 to be long enough for the operator to move away from the medical device treatment machine 10 before the door 14 is unlatched and automatically moved from the closed position to the open position (or is capable of being manually opened if automatic opening is not provided), so that the operator does not obstruct the opening of the door 14.

In the embodiment in which the foot-operated automatic door opening mechanism 90 is activated when the latch and lock assembly 30 is in the locked/latched state, upon receipt of the foot-removal signal, the controller 92 is configured to send an unlock signal, after a first predetermined period of time from receipt of the foot-removal signal, to the first actuator 56 of the latch and lock assembly 30 to move the locking tab 60 from the locked position to the unlocked position. After a second predetermined period of time from receipt of the foot-removal signal, for example a short time after the first predetermined period of time or otherwise after the latch and lock assembly 30 is unlocked, the controller 92 is configured to send the unlatch signal to the second actuator 58 to rotate the door opening tab 60 to pivot the lever 44 from the latched position to the unlatched position. The first and second predetermined periods of time may be configured by the controller 92 to be long enough for the operator to move away from the medical device treatment machine 10 before the door 14 is unlatched and automatically moved from the closed position to the open position (or is capable of being manually opened if automatic opening is not provided), so that the operator does not obstruct the opening of the door 14.

It will be appreciated, then, that the foot-operated automatic door opening mechanism 90 may be in any one of a ready state, an activated state or an automatic-opening state. The ready state is the default state of the foot-operated automatic door opening mechanism 90. In the ready state, the indicator apparatus 98 is in a first state. In the embodiment wherein the indicator apparatus 98 is a light indicator, the first state of the light indicator may either be unilluminated or may be illuminated in a first color. The first state of the indicator apparatus 98 indicates to the operator that the sensing apparatus 94 (for example, a proximity sensor or a pedal or lever) is ready for activation.

Upon activation of the sensing apparatus 94 by the foot of the operator, the activated state is reached. In the activated state, the indicator apparatus 98 is in a second state. In the embodiment wherein the indicator apparatus 98 is the light indicator, the second state of the light indicator may either be illuminated (where the first state was unilluminated) or may be illuminated in a second color (wherein the first state was illuminated in a first color). The second state of the indicator apparatus 98 indicates to the operator that the sensing apparatus 94 has been activated and that upon subsequent deactivation of the sensing apparatus 94, the latch and lock assembly 30 will be unlatched and the door 14 will be automatically opened after a predetermined period of time or after first and second predetermined periods of time, as the case may be.

Upon deactivation of the sensing apparatus 94 for example by the foot of the operator being out of sensing range of the proximity sensor in one embodiment or removal of the foot from the pedal or lever in the other embodiment, the automatic-opening state, or third state, is reached. In the automatic-opening state, in the embodiment in which the foot operated automatic door opening mechanism 90 transitions the latch and lock assembly 30 from the unlocked/latched state to the unlocked/unlatched state, the controller 92 is configured to wait for the respective predetermined period of time, before sending the respective unlatch signal to the second actuator 58 of the latch and lock assembly 30. Upon unlatching of the latch and lock assembly 30, the door 14 automatically opens (or is capable of being manually opened if automatic opening is not provided), for example in the manner previously described. In the embodiment in which the foot operated automatic door opening mechanism 90 transitions the latch and lock assembly 30 from the locked/latched state to the unlocked/latched state and from the unlocked/latched state to the unlocked/unlatched state, the controller 92 is configured to wait for the respective first and second predetermined periods of time before sending the respective unlock signal and unlatch signal to the first actuator 56 and the second actuator 58, respectively, of the latch and lock assembly 30. Upon unlocking and unlatching of the latch and lock assembly 30, the door 14 automatically opens (or is capable of being manually opened if automatic opening is not provided), for example in the manner previously described.

As indicated above, the controller 92 of the latch and lock assembly 30 is generally configured to carry out the overall control of the functions and operations of the first actuator 56, the second actuator 58, the sensing apparatus 94 and/or the indicator apparatus 98. The controller 92 may be a central processing unit (CPU), microcontroller, or microprocessor. The controller 92 may execute program code stored in a non-transitory computer readable medium, such as random access memory (RAM), a read-only memory (ROM), an erasable programmable read-only memory (EPROM or Flash memory), or any other suitable memory device incorporated into the medical device treatment machine 10, to carry out operation of the first actuator 56, the second actuator 58, the sensing apparatus 94 and/or the indicator apparatus 98. It will be apparent to a person having ordinary skill in the art of computer programming how to program the controller 92 to operate and carry out the functions associated with its respective devices and/or systems. Accordingly, details as to specific programming code have been left out for the sake of brevity. Also, while the code may be executed by the controller 92 in accordance with an exemplary embodiment, such functionality may also be carried out via dedicated hardware, firmware, software, or combinations thereof, without departing from the scope of the invention.

Figure 7:
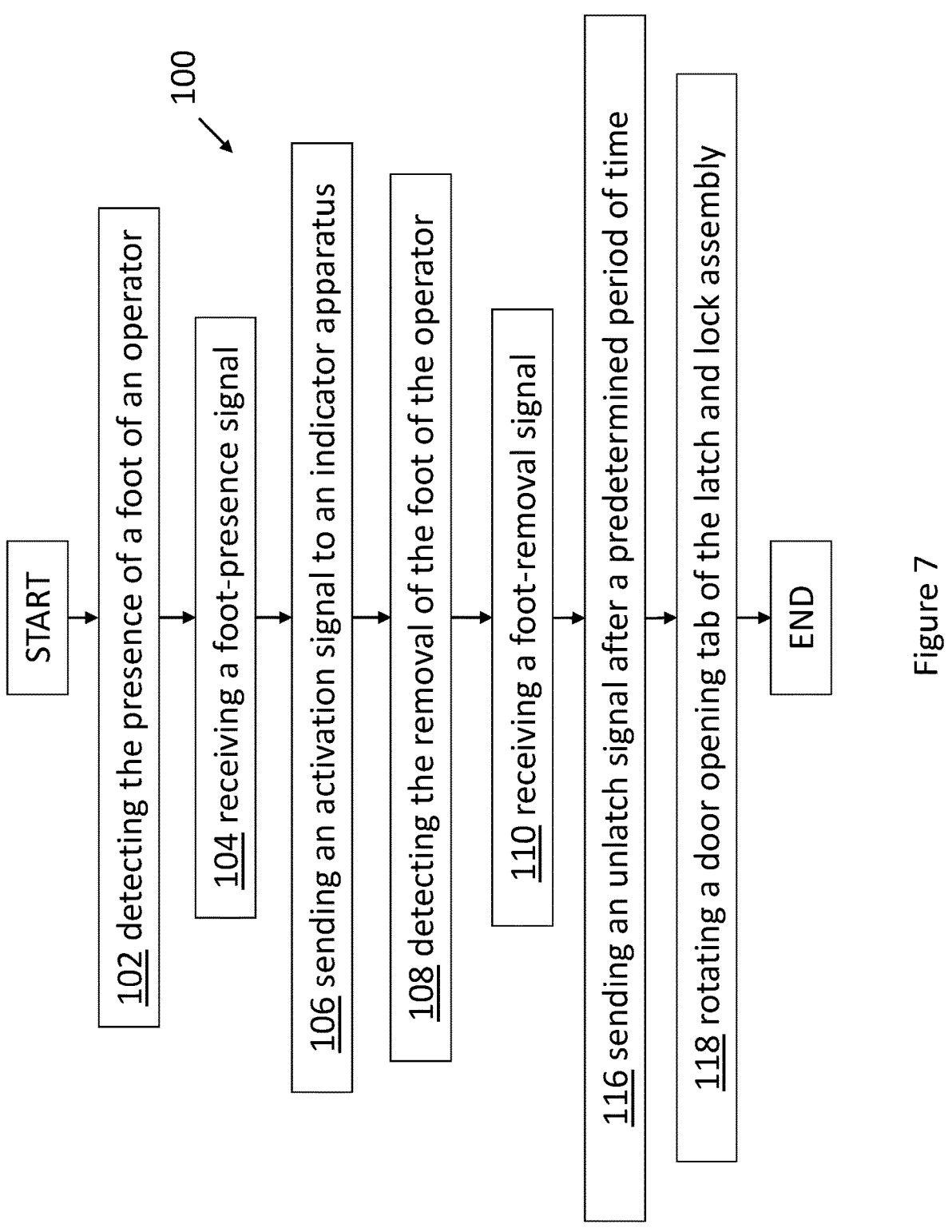
FIG. 7 is a flow chart of a method of operating a medical device treatment machine according to an aspect of the present invention.

With reference to FIG. 7, a method 100 of operating a medical device treatment machine 10 is provided. The method 100 includes, at step 102, detecting, by a sensing apparatus, such as for example a proximity sensor or a pedal or lever disposed on the medical device treatment machine, the presence of a foot of an operator in a sensing zone of the sensing apparatus. The method 100 then includes, at step 104, receiving, by a controller of the medical device treatment machine, a foot-presence signal from the sensing apparatus.

At step 106, the method 100 includes sending, by the controller, an activation signal to an indicator apparatus of the medical device treatment machine to activate the indicator apparatus. In an embodiment, the indicator apparatus may be a light indicator and the activation signal may be an illumination signal to illuminate the light indicator. In another embodiment, the activation signal may be an illumination color-change signal to change an illumination color of the light indicator. Other embodiments are also contemplated, as previously described.

At step 108, the method 100 further includes detecting, by the sensing apparatus, a removal of the foot of the operator from the sensing zone of the sensing apparatus. The method 100 then includes at step 110, receiving, by the controller, a foot-removal signal from the sensing apparatus.

The method 100 includes sending, at step 116, by the controller, an unlatch signal after a predetermined period of time upon receipt of the foot-removal signal. The controller sends the unlatch signal to an actuator, for example the afore described second actuator 58 of the latch and lock assembly. The method 100 then includes, at step 118, rotating, by the actuator, a door opening tab of the latch and lock assembly that is in abutting contact with a lever to pivot the lever from a latched position to an unlatched position. The method 100 may additionally include automatically moving a door of the medical device treatment machine from a closed position to an open position via a biasing force of a hinge of the door by a hinge biasing member.

In another embodiment, depicted in FIG. 8, prior to step 116, the method 100 may include sending, at step 112, by the controller, an unlock signal after a first predetermined period of time from receipt of the foot removal signal. The controller sends the unlock signal to a first actuator of the latch and lock assembly of the medical device treatment machine. At step 114, the method 100 may then include moving, by the first actuator, a locking tab of the latch and lock assembly from a locked position to an unlocked position. The sending, at step 116, by the controller of the unlatch signal may occur, therefore, at a second predetermined period of time after receipt of the foot-removal signal and after the first predetermined period of time at which the unlock signal is sent.

In another embodiment, a non-transitory computer-readable medium storing program code is provided. When the program code is executed, the non-transitory computer-readable medium is configured to perform the steps of the method previously described.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A medical device treatment machine comprising:
a treatment chamber for washing, disinfecting, and/or sterilizing a medical device,
a door hingedly attached to the treatment chamber and moveable between an open position, to expose the treatment chamber, and a closed position, to seal the treatment chamber, wherein the door comprises a latch pin on a first side of the door, and
a latch and lock assembly fixed to a wall of the treatment chamber, wherein the latch and lock assembly comprises:
a lever pivotable between a latched position and an unlatched position, wherein in the latched position, the lever engages the latch pin to prevent movement of the door from the closed position to the open position, and wherein in the unlatched position, the lever disengages the latch pin to allow movement of the door from the closed position to the open position,
a first actuator configured to selectively move a locking tab between a locked position and an unlocked position, wherein in the locked position, the locking tab is configured to block pivotable movement of the lever from the latched position to the unlatched position, and wherein in the unlocked position, the locking tab is configured to allow pivotable movement of the lever from the latched position to the unlatched position, and
a second actuator configured to selectively rotate a door opening tab between a first position and a second position when the locking tab is in the unlocked position, wherein when the door opening tab is in the first position the lever is in a latched position, and wherein when the door opening tab is rotated from the first position to the second position, the door opening tab abuts the lever and urges the lever from the latched position to the unlatched position.

2. The medical device treatment machine according to claim 1, further comprising a hinge on a second side of the door opposite the first side of the door.

3. The medical device treatment machine according to claim 2, wherein the hinge of the door comprises a hinge biasing member for biasing the door toward an open position to automatically move the door from the closed position to the open position when the lever is in the unlatched position.

4. The medical device treatment machine according to claim 1, further comprising:

a stop pin extending from the chamber, and a stop block fixed to the door, the stop block comprising a roller pin extending from the stop block in a direction configured to be perpendicular to the stop pin when the door is in a closed position, wherein when the door is in a closed position, the roller pin slidably abuts the stop pin to permit a lateral movement of the door between the closed position and the open position and block a vertical movement of the door in a direction perpendicular to the lateral movement of the door.

5. The medical device treatment machine according to claim 1, further comprising:

a sensing apparatus for detecting a presence and removal of a foot of an operator in a sensing zone of the sensing apparatus, and a controller for controlling the operations of the second actuator according to the detection of the presence and removal of the foot of the operator in the sensing zone of the sensing apparatus.

6. The medical device treatment machine according to claim 5, wherein the controller is configured to:

receive a foot-presence signal from the sensing apparatus when the sensing apparatus detects the presence of the foot of the operator in the sensing zone of the sensing apparatus, send an activation signal to an indicator apparatus on the medical device treatment machine to activate the indicator apparatus, receive a foot-removal signal from the sensing apparatus when the foot sensor detects the removal of the foot of the operator from the sensing zone of the sensing apparatus, and send an unlatch signal to the second actuator to rotate the door opening tab in abutting contact with the lever to pivot the lever from the latched position to the unlatched position.

7. The medical device treatment machine according to claim 6, wherein the controller is configured to send the unlatch signal to the second actuator a predetermined period of time after receipt of the foot-removal signal.

8. A method of operating a medical device treatment machine according to claim 6, comprising the steps of:

detecting, by the sensing apparatus disposed on the medical device treatment machine, the presence of the foot of the operator in the sensing zone of the sensing apparatus, receiving, by the controller of the medical device treatment machine, the foot-presence signal from the sensing apparatus, sending, by the controller, the activation signal to the indicator apparatus on the medical device treatment machine to activate the indicator apparatus, detecting, by the sensing apparatus, the removal of the foot of the operator from the sensing zone of the sensing apparatus, receiving, by the controller, the foot-removal signal from the sensing apparatus, sending, by the controller, the unlatch signal to the second actuator of the latch and lock assembly of the medical device treatment machine, and rotating, by the second actuator, the door opening tab of the latch and lock assembly that is in abutting contact with the lever to pivot the lever from the latched position to the unlatched position.

9. The method of operating the medical device treatment machine according to claim 8, wherein the unlatch signal is sent to the actuator a predetermined period of time after receipt of the foot-removal signal.

10. The method of operating the medical device treatment machine according to claim 8, further comprising:

automatically moving a door of the medical device treatment machine from a closed position to an open position via a biasing force on a hinge of the door by a hinge biasing member.

* * * * *